(12) United States Patent
Lund et al.

(10) Patent No.: US 6,183,445 B1
(45) Date of Patent: *Feb. 6, 2001

(54) SYRINGE WITH RETRACTABLE NEEDLE GUARD

(75) Inventors: Per William Lund, Fennevangen; Knud Robert Petersen, Vitus Berings Allé, both of (DK)

(73) Assignee: Radiometer Medical A/S, Bronshoj (DK)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/947,443

(22) Filed: Sep. 17, 1997

Related U.S. Application Data

(63) Continuation of application No. PCT/DK96/00100, filed on Mar. 14, 1996.

(30) Foreign Application Priority Data

Mar. 17, 1995 (DK) .................................................. 0270/95

(51) Int. Cl.⁷ ..................................................... A61M 5/32
(52) U.S. Cl. .......................................... 604/198; 604/192
(58) Field of Search ................................... 604/192, 195, 604/197, 198, 187, 110, 263, 162, 218, 171

(56) References Cited

U.S. PATENT DOCUMENTS

| 4,664,654 | * | 5/1987 | Strauss | 604/198 |
| 4,894,055 | * | 1/1990 | Sudnak | 604/198 |
| 4,923,447 | | 5/1990 | Morgan . | |
| 5,219,333 | * | 6/1993 | Sagstetter et al. | 604/198 |
| 5,232,457 | * | 8/1993 | Grim | 604/198 |
| 5,314,414 | * | 5/1994 | Hake et al. | 604/198 |
| 5,318,547 | | 6/1994 | Altschuler . | |
| 5,328,473 | * | 7/1994 | Fayngold et al. | 604/198 |
| 5,385,557 | | 1/1995 | Thompson . | |
| 5,389,085 | * | 2/1995 | D'Alessio et al. | 604/198 |
| 5,415,645 | * | 5/1995 | Friend et al. | 604/198 |
| 5,417,660 | * | 5/1995 | Martin | 604/269 |
| 5,472,430 | * | 12/1995 | Vaillancourt et al. | 604/198 |
| 5,498,243 | * | 3/1996 | Vallelunga et al. | 604/198 |
| 5,527,294 | * | 6/1996 | Weatherford et al. | 604/198 |
| 5,658,257 | * | 8/1997 | Ryles | 604/198 |
| 5,688,241 | * | 11/1997 | Asbaghi | 604/110 |
| 5,709,669 | * | 1/1998 | Haining | 604/198 |

FOREIGN PATENT DOCUMENTS

0350186A * 1/1990 (EP) ..................................... 604/198

* cited by examiner

*Primary Examiner*—Sharon Kennedy
(74) *Attorney, Agent, or Firm*—Bryan Cave LLP (57) ABSTRACT

The present invention is directed to a syringe with a retractable needle guard. The syringe has two coaxial tubular bodies, an inner and an outer body, which are adapted to telescope in relationship to each other. The outer tubular body is adapted to at least partially receive the body of the container from which fluid is to be drawn and the inner tubular body is adapted to be displaced from a retracted position to an advanced position. In the retracted position the needle is exposed, while in the advanced position the needle is surrounded by the inner tubular body. The syringe with a retractable needle guard may also be adapted to connect the outer tubular body with the needle without connecting it to the container from which fluid is to be drawn.

24 Claims, 7 Drawing Sheets

SYRINGE WITH RETRACTABLE NEEDLE GUARD

This is a continuation of International Application No. PCT/DK96/00100 filed Mar. 14, 1996.

BACKGROUND OF THE INVENTION

The present invention relates to a shielding means for a needle of a container-needle assembly comprising a container having an elongate body, a needle and connecting parts for connecting the container releasably with the needle, said shielding means comprising two coaxial tubular bodies, an inner and an outer body, which are made to telescope in relation to each other. The outer tubular body is adapted to at least partially receive the body of the container, and the inner tubular body is adapted to be displaced from a retracted position in which the needle is exposed, to an advanced position in which the needle is surrounded by the inner tubular body.

The invention further relates to a container-needle assembly comprising a container having an elongate body, a needle and connecting parts connecting the container releasably with the needle and comprising a shielding means having two coaxial tubular bodies, an inner and an outer body, which are made to telescope in relation to each other. The outer tubular body is adapted to at least partially receive the body of the container, and the inner tubular body is adapted to be displaced from a retracted position, in which the needle is exposed, to an advanced position, in which the needle is surrounded by the inner tubular body.

In connection with blood sampling by means of puncture where a needle connected with a sample container is connected to a patient's bloodstream, there is a risk of accidental needle-stick to the user. This risk also exists in connection with injection of e.g. medicine where a fluid in a sample container is transferred to a patient via a needle. It is therefore desired to be able to shield the used needle without the user getting in contact with the needle. For that purpose, several different shielding means and container-needle assemblies as described in the opening part have been developed.

Thus, U.S. Pat. No. 4,923,447 (Morgan) and U.S. Pat. No. 5 318 547 (Altschuler) disclose shielding means comprising two coaxial tubular bodies, an inner and an outer body, which are made to telescope in relation to each other, the outer of which is adapted to receive the container of a container-needle assembly and to be secured to the far end of said container relative to the needle. An operation projection at the inner tubular body extends through a longitudinal slot of the outer tubular body and may be operated by a user in order to displace the inner tubular body to an advanced position in which it surrounds and shields the needle.

Said known shielding means are thus connected with the container-needle assembly at the far end of the container relative to the needle. However, during e.g. blood sampling it is preferable after usage of the container-needle assembly to be able to remove the container with the withdrawn blood sample from the other part of the container-needle assembly, thus facilitating the handling of the blood sample. Such a removal is not possible in connection with the known shielding means.

SUMMARY OF THE INVENTION

It is therefore an object of the invention to provide a shielding means and a container-needle assembly as described in the opening part in order to enable removal of the container from the other part of the container-needle assembly.

This is achieved by means of a shielding means of the type described in the opening part which is characteristic by connection means for connecting said outer tubular body with the needle without connecting to the container. It is thereby achieved that the shielding means, when connected to a container-needle assembly, is connected to the needle which, at a later stage, is to be shielded without preventing the removal of the container.

In an embodiment where the connecting parts between the container and the needle comprise a connecting piece at one end of the body of the container and a hub part on the needle for receiving the connecting piece, the connection means is preferably adapted for connecting said outer tubular body with said hub part. Thus, the connection means comprises preferably an annular shoulder and means for engaging with and retaining the hub part when positioned at said shoulder. An embodiment is thus achieved which may be applied in connection with a sampler and a common, commercially available needle. Other suitable connection means or connectors comprise threads, press fits, bayonet joints and weldings, e.g. ultrasonic weldings, etc.

Alternatively, the connecting parts between the container and the needle may comprise a single part, e.g. a rubber membrane closing the container at the needle end of the container. In this case, the needle is preferably designed as a double-ended needle comprising a point in both ends, the needle being retained by the connection means, and the membrane is pierced by the needle so that the needle points are located on each side of the membrane when the container-needle assembly and the shielding means are assembled.

In an embodiment where an operation means extends from one end of the inner tubular body through a longitudinal slot of the outer tubular body, the connection means is preferably connected with one end of the outer tubular body through a narrow intermediate piece extending through a longitudinal slot of the inner tubular body.

The object is also achieved by means of a container-needle assembly of the type mentioned in the opening part which is characteristic of connection means for connecting said outer tubular body with the needle without connecting to the container. Such a container-needle assembly may be ready-made and be sterilized by the manufacturer and delivered to the user ready for use.

BRIEF DESCRIPTION OF THE DRAWINGS

The invention is further described by means of an embodiment with reference to the drawing, wherein.

DETAILED DESCRIPTION OF THE DRAWINGS

Figure 1:
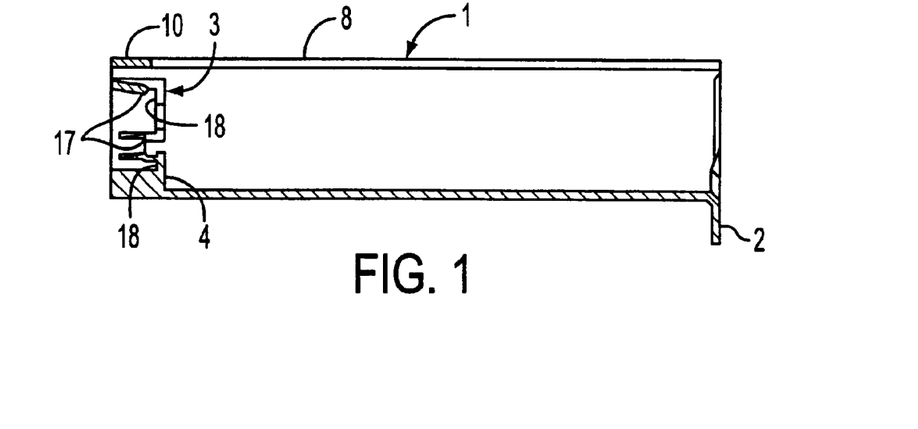
FIG. 1 shows a section through the outer tubular body of the shielding means.
Figure 2:
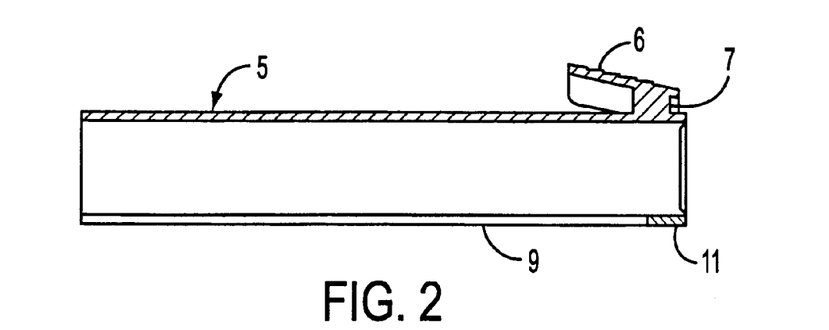
FIG. 2 shows a section through the inner tubular body.
Figure 3:
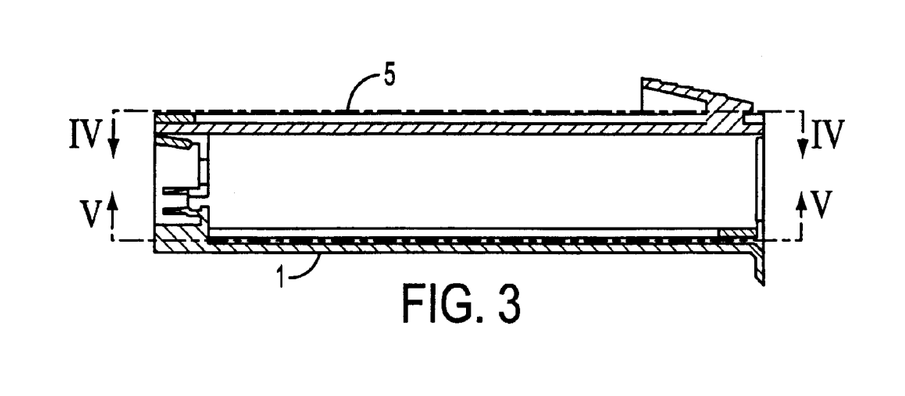
FIG. 3 shows a section through the outer and inner tubular body when assembled, as shown by the line III—III of FIG. 6.
Figure 4:
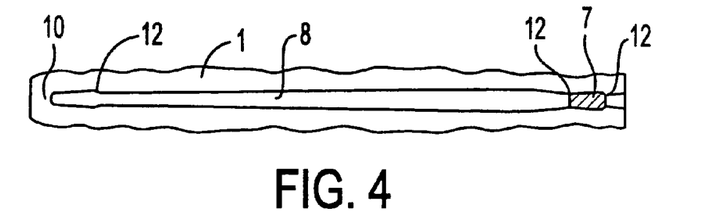
FIG. 4 shows a partial section along the line IV—IV of FIG. 3.
Figure 5:
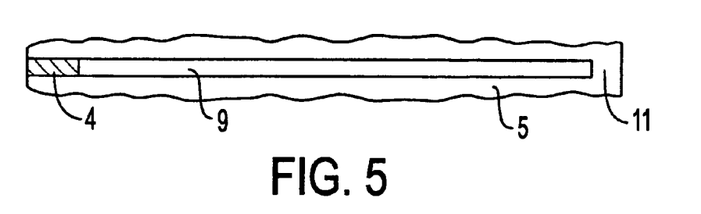
FIG. 5 shows a partial section along the line V—V of FIG. 3.
Figure 6:
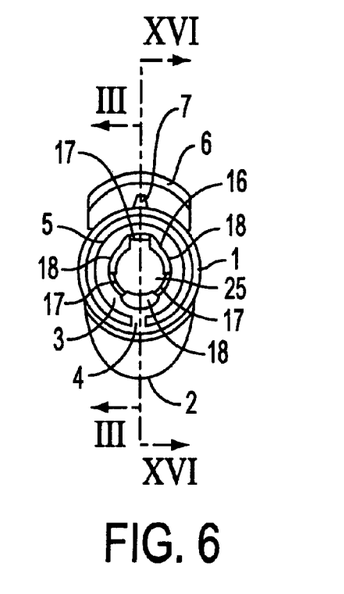
FIG. 6 shows the assembled outer and inner tubular body seen from the left side of FIG. 3.

The shielding means shown in FIGS. 1–6 and 14 comprises an outer tubular body 1, one end of which is provided with a finger tab 2 and the other end of which is provided with a connection means 3 for a needle. The connection means 3 is connected with the remaining part of the outer tubular body 1 through a narrow intermediate piece 4. The shielding means further comprises an inner tubular body 5, one end of which is provided with an operation button 6, connected with the inner tubular body 5 through a second intermediate piece 7. The two tubular bodies 1 and 5 are each provided with a longitudinal slot 8 and 9, respectively, extending through said entire tubular body, except for a small piece 10 and 11, respectively, in one end. Because the slots 8, 9 are open in the other ends opposite to the small pieces 10, 11, it is possible to push together the two tubular bodies 1, 5 as shown in FIG. 3. Thus, the intermediate piece 4 extends through the slot 9 and the intermediate piece 7 extends through the slot 8 as appears from FIGS. 4 and 5. The intermediate piece 4 (see FIG. 5) has an essentially rectangular cross section whereas the intermediate piece 7 (see FIG. 4) has a wedge-shaped cross section, and the slot 8 is provided with indentations 12 thus establishing a stop for the intermediate piece 7 at each end of the slot 8. It is thereby achieved that the position of the inner tubular body 5 relative to the outer tubular body 1 may be retained, both in the retracted position shown in FIG. 3, and in the advanced position shown in FIGS. 11 and 12. Due to the wedge-shape of the intermediate piece 7 there is a relatively weak detention against movement from the retracted position shown in FIG. 3 towards the advanced position shown in FIGS. 11 and 12, whereas there is a stronger detention against movement in the opposite direction, which is requirable, as described further below.

Figure 15:
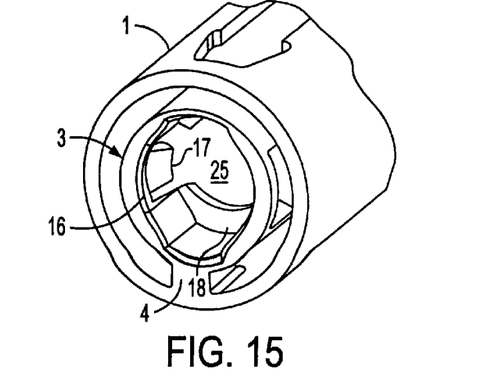
FIG. 15 shows an enlarged section of FIG. 14 showing one end of the outer tubular body.
Figure 16:
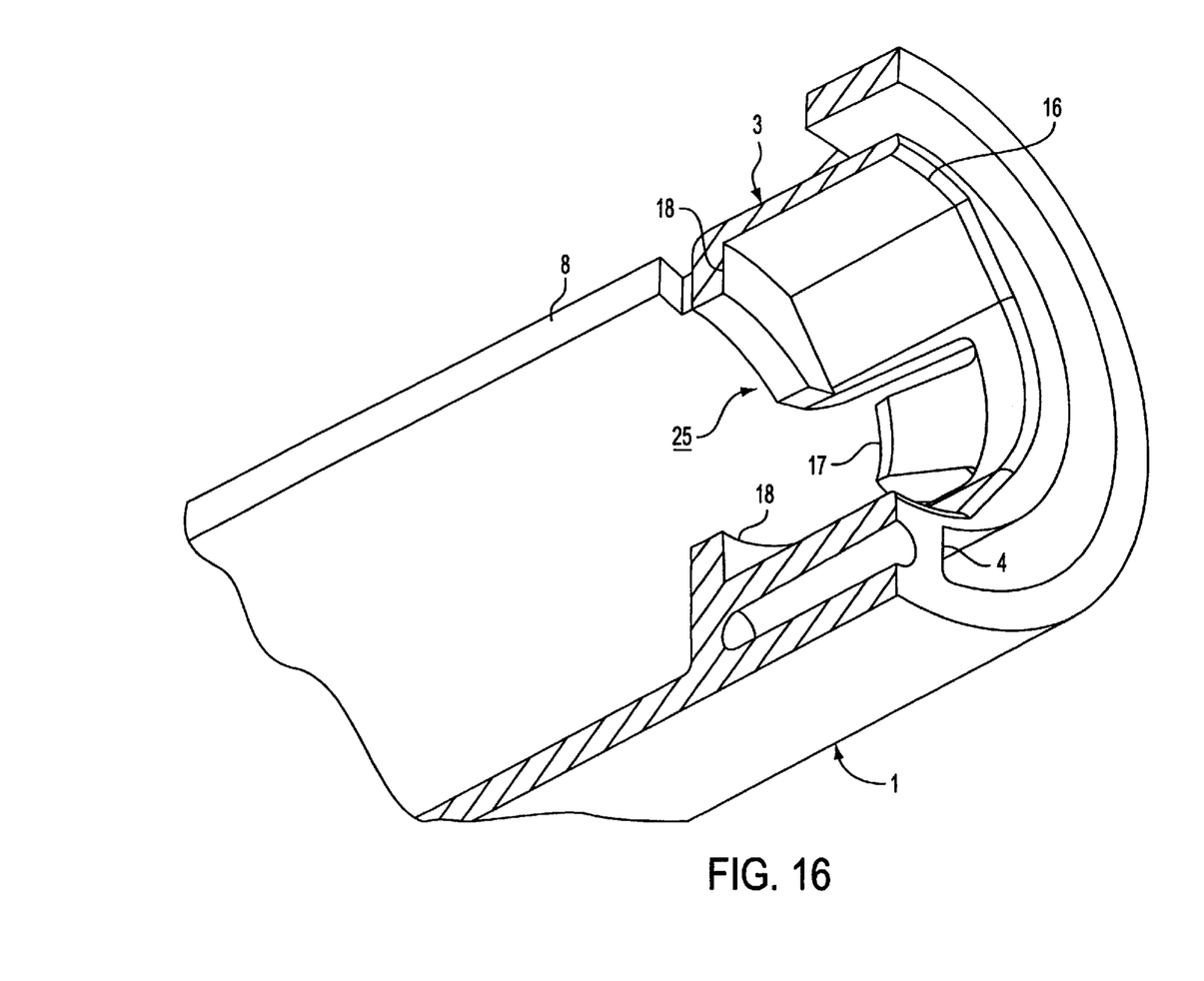
FIG. 16 shows a perspective section through the same end of the outer tubular body as shown by the arrows XVI—XVI of FIG. 6.

The connection means 3, which is shown most clearly in FIGS. 15 and 16, is in the embodiment shown designed to receive a common, commercially available needle 13 provided with a conical hub 14 with a hub collar 15 (see FIGS. 7 and 9–12). Thus, the-connection means 3 is shaped like a cup with a hole 25 in the bottom and an internal opening whose profile 16 corresponds to the circumference of the hub collar 15. Inside the cup the connection means 3 is provided with two (FIGS. 14, 15 and 16) or three (FIGS. 1–6) inwardly extending, resilient tabs 17 adapted to provide a snap lock engagement with the hub collar 15 as appears from FIGS. 7 and 9–12. The hub collar 15 is thereby retained between a shoulder 18 constituted by the other part of the bottom of the cup and the tabs 17.

Figure 7:
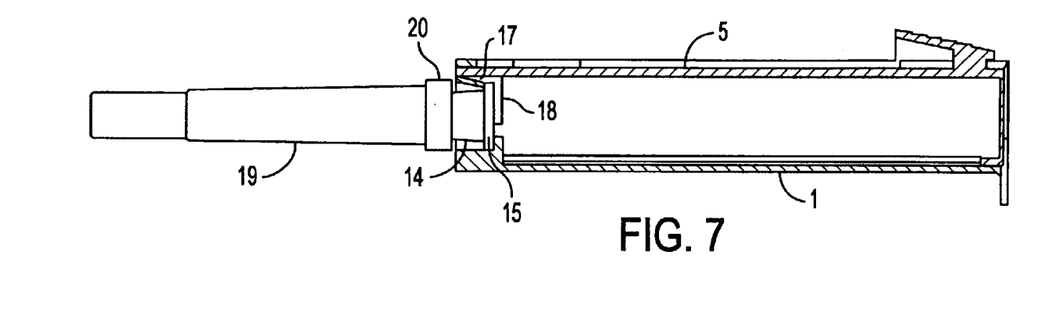
FIG. 7 shows a partially sectional view of the assembled outer and inner tubular body provided with a capped needle.

FIG. 7 shows the shielding means of FIG. 3 provided with a needle which again is provided with a protection cap 19, thereby revealing only the hub 14 of the needle. The protection cap 19 shown is a common, commercially available cap with a collar 20 preventing the protection cap from being moved through the hole 25 of the connection means 3, and accordingly the needle must be mounted from the left side of the figures, but in connection with another needle with a protection cap designed differently it may be possible to mount the needle from the right side of the figures, i.e. the entire needle with the protection cap is moved through the tubular bodies and secured in the connection means 3 which in that case is adapted to receive the needle from that side.

Figure 8:
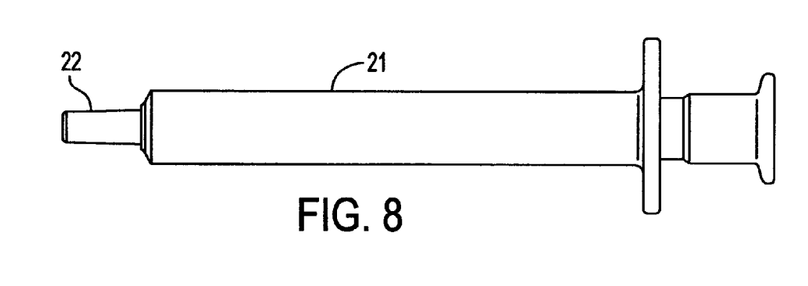
FIG. 8 shows a blood sampler.
Figure 9:
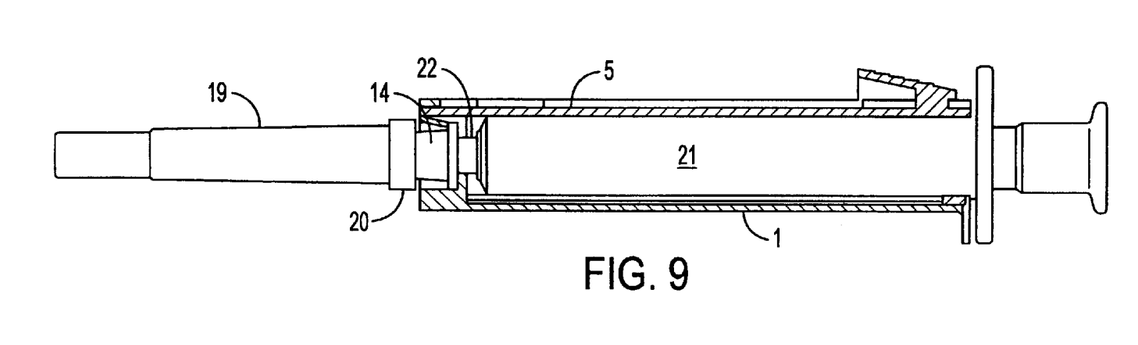
FIG. 9 shows a view corresponding to FIG. 7, but having the blood sampler of FIG. 8 in position.

FIG. 8 shows the container part of a container-needle assembly, said container part may as an example be a special blood sampler having a container 21 and a connecting piece 22. FIG. 9 shows the sampler introduced into the shielding means and the connecting piece 22 received in the hub 14 of the needle 13 in order to connect the needle and sampler.

Figure 10:
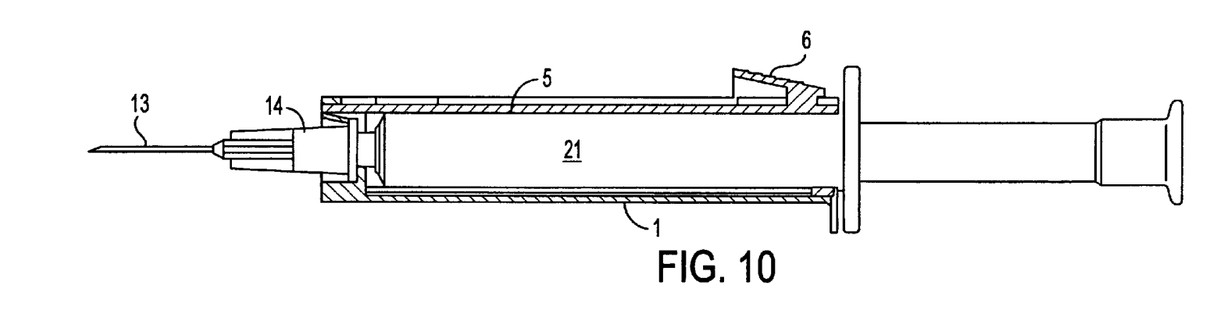
FIGS. 10–12 show a sequence of the handling of the device in connection with sampling.
Figure 13:
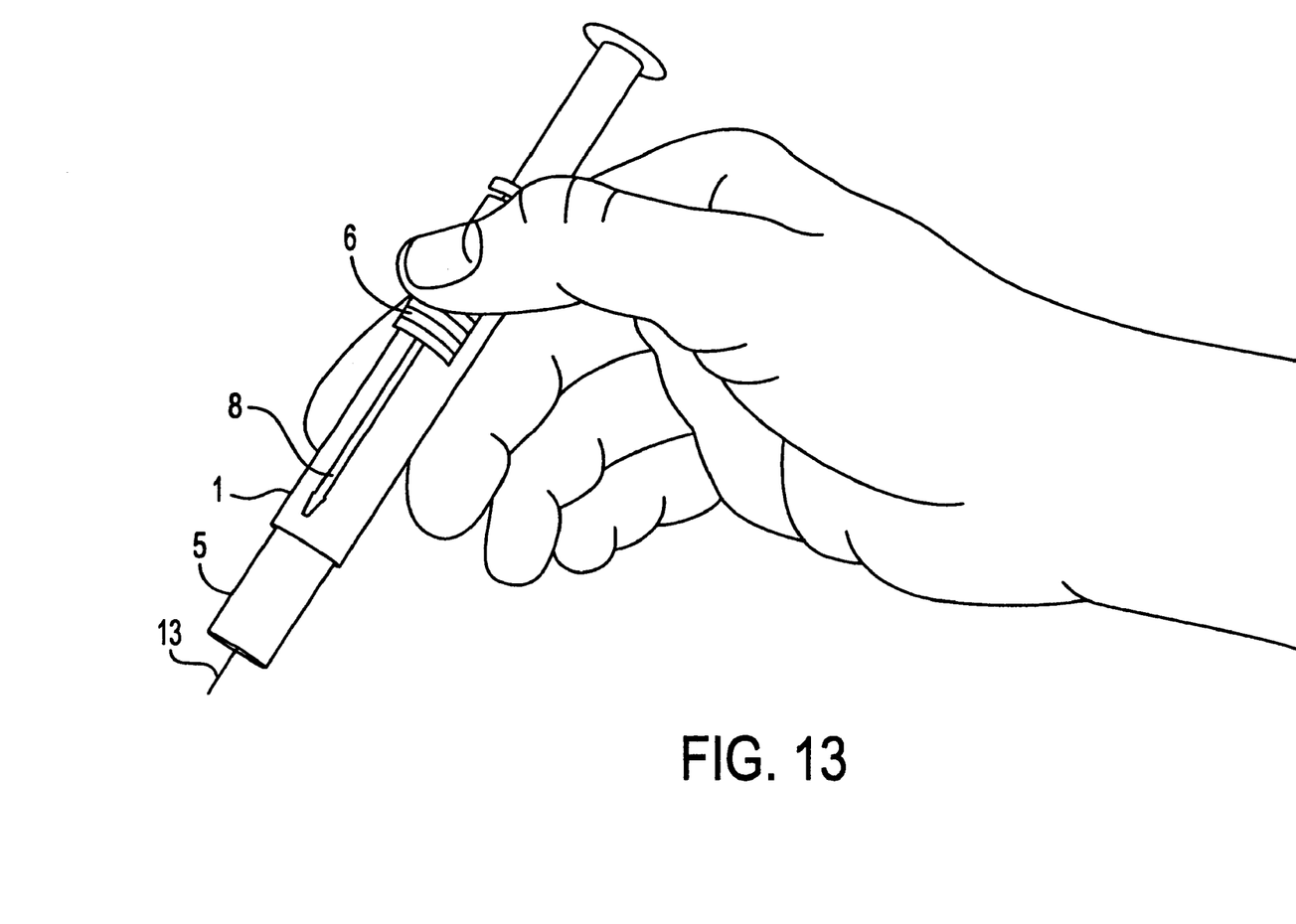
FIG. 13 shows a view indicating the handling of the shielding means.
Figure 14:
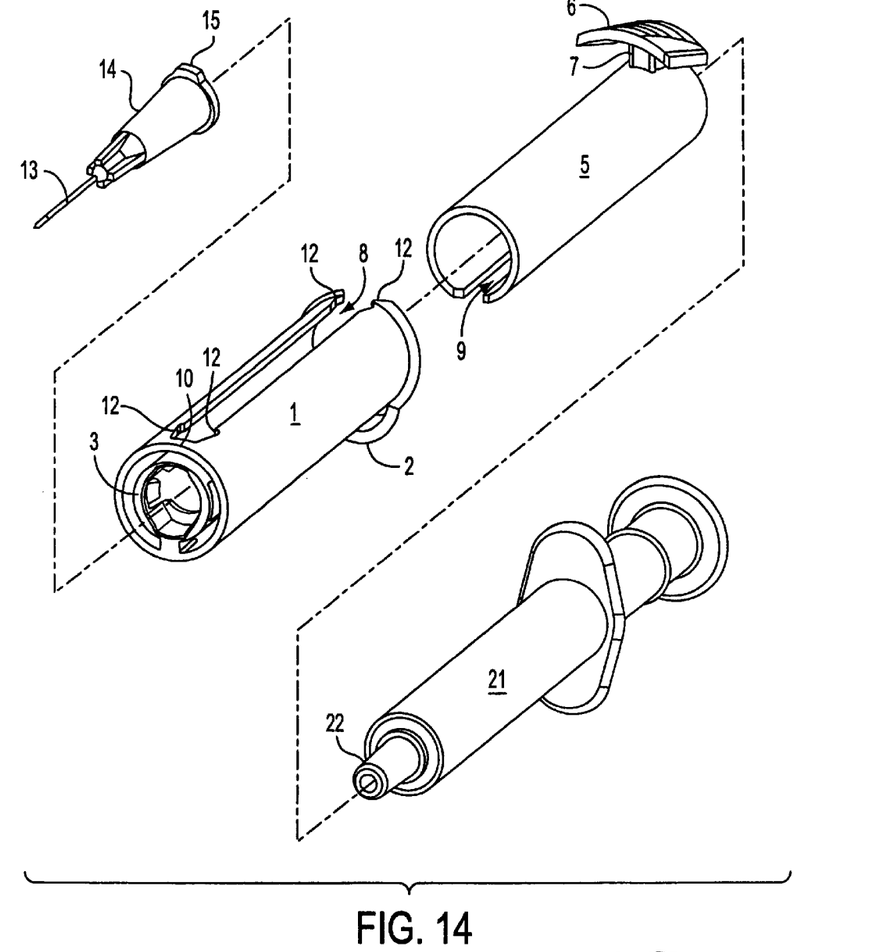
FIG. 14 shows an exploded perspective view of a container-needle assembly.

FIG. 10 shows the container-needle assembly of FIG. 9 upon blood sampling. At this stage, the protection cap 19 is removed from the needle, and to avoid the user of the sampler getting in contact with the needle point 13, the inner tubular body 5 is advanced to the position shown in FIG. 11 by means of the operation button 6. This is done by one single motion of hand as illustrated in FIG. 13.

Figures 11, 12:
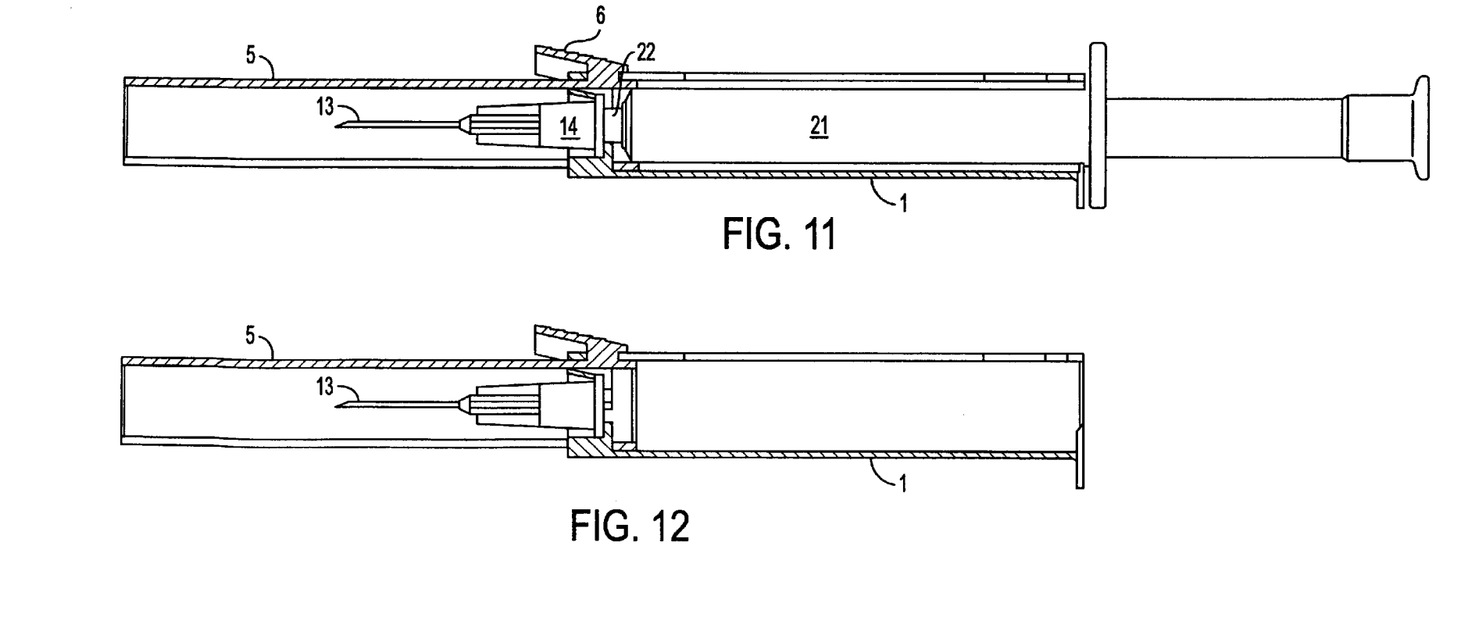

When the inner tubular body 5 is such advanced and the intermediate piece 7 is secured behind the indentations 12 at the near end of the slot relative to the needle, the sampler may be removed from the needle 13 and from the shielding means as shown in FIG. 12. When removing the sampler it is advantageous if the profile 16 of the opening of the connection means 3 corresponds to the profile of the hub collar 15, which preferably is not rotationally symmetric, as it is thus possible to turn the sampler relative to the needle 13 and thus facilitating the release of the sampler. Due to the pointed shape of the second intermediate piece 7, the inner tubular body 5 is retained with a relatively strong resistance against movement to the right in the FIGS. 15 by the indentations 12, the result of this being that the two tubular bodies cannot easily be separated (from the retracted position of the inner tubular body 5, see FIG. 3), and the inner tubular body 5 cannot easily be moved back from its advanced position (see FIGS. 11 and 12). It is thereby ensured that the used needle 13 is not unintentionally exposed. It is further ensured that the inner tubular body 5 is retained in its retracted position until the user wants to displace it to the advanced position, whereby only a weak force is needed to displace the inner tubular body 5 to the left in the figures from the retracted position.

The shielding means is preferably made of a polymeric material of some rigidity and preferably of a transparent material so that it is possible to observe the container when used. The rigidity (elastic modulus) of the material should preferably be in the range of 200 N/mm$^2$ to 5000 N/mm$^2$. Examples of applicable materials are polyethylene, polypropylene, polymethylpentene, polystyrene, modified compounds of styrene-polymers and polystyrene, polycarbonate, polymethylmethacrylate (acrylics), polyamide, polyvinylchloride, polyethylenterephthalate (polyester), including modified polyesters.

In a preferred embodiment the outer tubular body 1 is made of styrene/acrylonitrile copolymer, SAN, (BASF, Luran 368R) and the inner tubular body 5 is made of styrene/butadiene copolymer, S/B, (BASF Styrolux 637D). By using said two different materials for the tubular bodies 1 and 5 a smaller friction between said bodies is obtained.

A manufacturer of the shielding means described above may choose among several ways of delivering the shielding means to the user. One way is to deliver an assembled, sterilized unit comprising a container mounted with a needle onto which the shielding means is mounted. In this case, which is the preferred way, the shielding means and the needle need not be separable from each other, but may as an example be welded together by ultrasonic welding. Other ways are to deliver the shielding means alone or together with the container, but without the needle. In these cases, the connection means must be adapted to commonly available needles and the user himself has to mount the shielding means onto the needle and connect the needle with the container.

The use of the shielding means will now be explained in connection with arterial blood sampling by means of the blood sampler 21 which in the first case mentioned above is delivered having the needle 13 and the shielding means mounted. The user (e.g. a laboratory assistant) goes to the patient concerned with the sampler 21 being packed in a sterile packaging. The packaging contains the sampler provided with a needle of the correct size with a protection cap as well as the shielding means and a tipcap for the sampler. The user also brings along latex gloves, a swap, gauze and plaster. At the patient the method is as follows:

The user puts on the latex gloves.

The selected puncture site is washed with alcohol by means of the swap.

The sterile packaging is opened aseptically.

The plunger of the sampler 21 is set to the sample volume required.

The protection cap 19 is removed from the needle 13.

The artery is located using the index finger/middle finger of one hand. The puncture is performed by the other hand. In this connection it is important that the hub part 14 of the needle is visible in order to assess the first flash of the arterial blood.

The filling of the sampler 21 is monitored.

When the sampler 21 is filled, the needle is withdrawn and the puncture site is compressed with one hand.

By the other hand (FIG. 13) the inner tubular body 5 is displaced over the used needle 13, forwards to the front locked position.

Then the sampler 21 is turned to mix anticoagulant present in the blood sample taken.

When the puncture site has been compressed for the prescribed time, the gaze and plaster are applied.

The sampler is turned/withdrawn from the needle and the shielding means which along with the used needle is discarded with other sharp waste.

The tipcap is mounted onto the sampler which is carried to an analyzer.

The tipcap is then removed, a few drops of blood are spilled whereupon the blood is injected into the analyzer.

The used sampler is discarded along with other sharp waste and/or blood-contaminated waste.

It should be understood that even though the invention above is described in connection with a sampler having a central connecting piece, it may just as well be used in connection with a sampler whose connecting piece is located eccentrically relative to the center line of the sampler. Moreover, the "sampler" need not be a plunger sampler, but any sampling container comprising an elongate body whose one end is connected releasably with a needle may be used. The shielding means may also be applied in connection with other container-needle assemblies than for blood sampling, e.g. for injections.

What is claimed is:

1. A needle shielding means for shielding a needle of a container-needle assembly, the shielding means comprising:
    an inner coaxial tubular body and an outer coaxial tubular body, the inner tubular body having a first end and a second end and being slidably receivable in the outer tubular body in a telescoping relationship, the outer tubular body having a first end and a second end, the second end extending over at least a part of an elongated body of the container of the attachable container-needle assembly,
    connection means attached to the outer coaxial tubular body of the shielding means for connecting the shielding means to the needle of the container-needle assembly; and
    wherein the inner tubular body is adapted to be displaced from a retracted position in which the second end of the inner tubular body is within the interior of the outer tubular body whereby the needle of the container-needle assembly is exposed, to an advanced position in which the second end of the inner tubular body is extended from the interior of the outer tubular body so that the needle is surrounded by the inner tubular body.

2. A needle shielding means according to claim 1, wherein the connection means is adapted for connecting said outer coaxial tubular body with a hub of the needle.

3. A needle shielding means according to claim 2, wherein the connection means comprises an annular shoulder and an engaging means for engaging with and retaining the hub of the needle when positioned at the shoulder.

4. A needle shielding means according to claim 3, wherein the engaging means comprises resilient snap lock means.

5. A needle shielding means according to claim 1, wherein the connection means comprises a thread, a press fit, a bayonet joint or a welding.

6. A needle shielding means according to claim 1, wherein the outer coaxial tubular body and the inner coaxial tubular body each have a longitudinal slots an operation means extending from the second end of the inner tubular body through the longitudinal slot in the outer tubular body and the connection means being connected with one end of the outer tubular body through a narrow intermediate piece extending through the longitudinal slot of the inner tubular body.

7. A needle shielding means according to claim 2, wherein the connection means comprises a thread, a press fit, a bayonet joint or a welding.

8. A needle shielding means according to claim 7, wherein the connection means is an ultrasonic welding.

9. A needle shielding means according to claim 5, wherein the connection means is an ultrasonic welding.

10. A container-needle assembly with retractable shielding means comprising:
    a container having an elongated body,
    a needle secured to a connecting part, said connecting part connecting the container releasably to the needle,
    shielding means having an inner coaxial tubular body and an outer coaxial tubular body, the inner coaxial body having a first end and a second end and being slidably receivable in the outer tubular body in a telescoping relationship, the outer tubular body having a first end and a second end, the second end extending over at least a part of the elongated body of the container,
    connection means attached to the first end of the outer tubular body and connected to the connecting part of the needle, wherein the inner body is adapted to be displaced from a retracted position from the interior of the outer coaxial tubular body in which the needle is exposed to an advanced position in which the inner body is extended from the interior of the outer coaxial tubular body so that the needle is surrounded by the inner tubular body.

11. A container-needle assembly of claim 10, wherein said connection means comprises an annular shoulder and engaging means for engaging with and retaining the connecting part of the needle when positioned at said shoulder.

12. A container-needle assembly of claim 11, wherein the engaging means comprises resilient snap lock means.

13. A container-needle assembly of claim 11, wherein the connection means comprises a thread, a press fit, a bayonet joint or a welding.

14. A container-needle assembly according to claim 10, wherein the outer coaxial tubular body and the inner coaxial tubular body each have a longitudinal slot, an operation means extending from the second end of the inner tubular body through the longitudinal slot in the outer tubular body and the connection means being connected with one end of the outer tubular body through a narrow intermediate piece extending through the longitudinal slot of the inner tubular body.

15. A container-needle assembly according to claim 13, wherein the connection means is an ultrasonic welding.

16. A container-needle assembly comprising a container having an elongated body, a needle and connecting parts connecting the container releasably with the needle, and a needle shielding means comprising:

an inner coaxial tubular body and an outer coaxial tubular body, the inner tubular body having a first end and a second end and being slidably receivable in the outer tubular body in a telescoping relationship, the outer tubular body having a first end and a second end, the second end being adapted to extend over at least a part of the elongated body of the container, connection means attached to the outer tubular body and connected to the needle, wherein the inner tubular body is adapted to be displaced from a retracted position, in which the second end of the inner tubular body is within the interior of the outer tubular body and the needle is exposed, to an advanced position, in which the second end of the inner tubular body is extended from the interior of the outer tubular body and the needle is surrounded by the inner tubular body.

17. A container-needle assembly according to claim 16, wherein the connecting parts comprise a connecting piece at one end of the body of the container and a hub of the needle, the hub receiving the connecting piece, and wherein the connection means connects the outer tubular body with the hub of the needle.

18. A container-needle assembly according to claim 17, wherein the connection means comprises a thread, a press fit, a bayonet joint or a welding.

19. A container-needle assembly according to claim 17, wherein said connection means comprises an annular shoulder and an engaging means for engaging with and retaining the hub of the needle when positioned at the shoulder.

20. A container-needle assembly according to claim 19, wherein the engaging means comprises a resilient snap lock means.

21. A container-needle assembly according to claim 16, wherein the connection means comprises a thread, a press fit, a bayonet joint or a welding.

22. A container-needle assembly according to claim 16, wherein the outer coaxial tubular body and the inner coaxial tubular body each have a longitudinal slot, an operation means extending from the second end of the inner tubular body through the longitudinal slot in the outer tubular body and the connection means being connected with one end of the outer tubular body through a narrow intermediate piece extending through the longitudinal slot of the inner tubular body.

23. A container-needle assembly according to claim 21 wherein the connection means is an ultrasonic welding.

24. A container-needle assembly according to claim 18, wherein the connection means is an ultrasonic welding.

* * * * *

UNITED STATES PATENT AND TRADEMARK OFFICE
CERTIFICATE OF CORRECTION

PATENT NO. : 6,183,445 B1  Page 1 of 1
DATED : February 6, 2001
INVENTOR(S) : Per William Lund and Knud Robert Peterson It is certified that error appears in the above-identified patent and that said Letters Patent is hereby corrected as shown below:

Title page,
Item [75], Inventors, the cities of residence of the inventors are incorrect. Therefore, please change "Fennevangen" to -- Gentofte -- and "Alle" to -- Klampenborg --;

Column 6,
Line 38, please change "slots" to -- slot --;

Column 7,
Line 12, please change "11" to -- 10 --.

Signed and Sealed this

Nineteenth Day of February, 2002

Attest:

JAMES E. ROGAN
Attesting Officer   Director of the United States Patent and Trademark Office